United States Patent
Cai et al.

(10) Patent No.: US 9,725,529 B2
(45) Date of Patent: *Aug. 8, 2017

(54) COMPOSITIONS AND METHODS FOR MAKING AND USING MULTIFUNCTIONAL POLYMERIZED LIPOSOMES

(71) Applicant: University of Houston, Houston, TX (US)

(72) Inventors: Chengzhi Cai, Houston, TX (US); Guoting Qin, Houston, TX (US); Amit Kumar, Houston, TX (US)

(73) Assignee: UNIVERSITY OF HOUSTON, Houston, TX (US)

( * ) Notice: Subject to any disclaimer, the term of this patent is extended or adjusted under 35 U.S.C. 154(b) by 486 days.

This patent is subject to a terminal disclaimer.

(21) Appl. No.: 13/894,101

(22) Filed: May 14, 2013

(65) Prior Publication Data

US 2013/0324738 A1    Dec. 5, 2013

Related U.S. Application Data

(63) Continuation of application No. 12/191,946, filed on Aug. 14, 2008, now Pat. No. 8,506,993.

(60) Provisional application No. 60/955,811, filed on Aug. 14, 2007.

(51) Int. Cl.
  *C08F 4/04* (2006.01)
  *A61K 9/127* (2006.01)
  *A61K 47/48* (2006.01)
  *A61K 49/00* (2006.01)
  (Continued)

(52) U.S. Cl.
  CPC .............. *C08F 4/04* (2013.01); *A61K 9/1271* (2013.01); *A61K 9/1277* (2013.01); *A61K 47/48815* (2013.01); *A61K 49/0002* (2013.01); *A61K 49/0021* (2013.01); *A61K 49/0043* (2013.01); *A61K 49/0084* (2013.01);
  (Continued)

(58) Field of Classification Search
  None
  See application file for complete search history.

(56) References Cited

U.S. PATENT DOCUMENTS 8,426,028 B2 *    4/2013  Cai .................. G01N 33/50
                                                  428/220
8,506,993 B2 *    8/2013  Cai ...................... A61K 9/1271
                                                  424/450

(Continued)

OTHER PUBLICATIONS

G Molteni, P De Buttero. "1,3-Dipolar cycloadditions of MeOPEG-bounded azides." Tetrahedron, vol. 61, 2005, pp. 4983-4987.*

(Continued)

*Primary Examiner* — Isaac Shomer
(74) *Attorney, Agent, or Firm* — Winstead PC

(57) ABSTRACT

According to some embodiments, the present invention provides compositions and methods for making and using multifunctional polymerized liposomes finding relevant application in medical sciences, particularly in bioimaging, diagnostics, drug delivery, and drug formulation. The compositions and methods involve lipids that are both polymerizable and have a "clickable" group that provides the ability to functionalize via a click reaction with various functional moieties useful for the above-listed applications.

3 Claims, 8 Drawing Sheets

(51) Int. Cl.
*C08F 30/02* (2006.01)
*B01J 31/18* (2006.01)
(52) U.S. Cl.
CPC ........... *B01J 31/1815* (2013.01); *C08F 30/02* (2013.01); *B01J 2231/44* (2013.01); *B01J 2531/16* (2013.01)

(56) References Cited

U.S. PATENT DOCUMENTS

| | | | |
|---|---|---|---|
| 8,927,733 B2* | 1/2015 | Cai | B82Y 30/00 548/109 |
| 2005/0048650 A1* | 3/2005 | Ignatious | A61K 9/127 435/458 |

OTHER PUBLICATIONS

VV Rostovtsev, LG Green, VV Fokin, KB Sharpless. "A Stepwise Huisgen Cycloaddition Process: Copper(I)-Catalyzed Regioselective "Ligation" of Azides and Terminal Alkynes." Angewandte Chemie vol. 114 No. 14, 2002, pp. 2708-2711.*

RJ Amir, E Danieli, D Shabat. "Receiver-Amplifier, Self-Immolative Dendritic Device." Chemistry a European Journal, vol. 13, 2007, pp. 812-821, published online Oct. 31, 2006.*

* cited by examiner

GENERAL FORMULA:  R¹, R² = H, ALKYL, OR SUBSTITUTED ALKYL, E.G.

R³ = COOH, OR' (R'=H, CH₃), OR SUBSTITUTED ALKYL, E.G.
$(CH_2CH_2O)_nR''$ (R'' = H, CH₃, n = 1 - 30)
m = 1-3

EXAMPLES:

6

7

8

9

10

11

90%
18

87%
19

=R

COMPOSITIONS AND METHODS FOR MAKING AND USING MULTIFUNCTIONAL POLYMERIZED LIPOSOMES

CROSS-REFERENCE TO RELATED APPLICATION

This application claims priority to U.S. patent application Ser. No. 12/191,946, to Cai, et al., entitled Compositions and Methods for Making and Using Multifunctional Polymerized Liposomes", filed Aug. 14, 2008, which claims priority to U.S. Provisional Application No. 60/955,811, to Cai, et al., entitled "Method for Making and Using Multifunctional Polymerized Liposomes", filed Aug. 14, 2007, each hereby incorporated herein by reference.

STATEMENT OF FEDERAL GOVERNMENT SPONSORSHIP

Not applicable.

FIELD OF THE INVENTION

The present invention relates to compositions and methods for making multifunctional polymerized liposomes.

BACKGROUND

Multifunctional polymerized liposomes have been proposed for applications in medical sciences, such as bioimaging, diagnostics, drug delivery, and drug formulation. The multifunctional polymized liposomes have various functional moieties attached to a liposome core.

Methods have been described to prepare multiple functional polymerized liposomes with functional moieties that are either incorporated in the building blocks of the liposomes, or attached to an avidin moiety that binds to biotinated liposomes. In the case where functional moieties are incorporated in the liposome's building blocks, the ratio and density of the imaging and targeting agents in the polymerizable liposomes are limited by the phase diagram of the system.

However, when the functional moieties are attached to the avidin bound onto biotinylated liposomes, the loading is limited by the large size of avidin on the polymerizable liposome surface. Covering liposomes with avidin also increases non-specific binding and reduces the circulation time, both being important drawbacks for drug delivery, for example.

More recently, clickable liposomes have been described. However, in such cases, the liposomes were not polymerizable, and therefore not stable. The lack of stability significantly limits the development of non-polymerizable clickable liposomes for potentially relevant biomedical applications, as most liposomes used for diagnosis and drug delivery require a systematic optimization of the composition and density of many functional moieties on the liposome, which is challenging—if not impossible—to achieve on unstable non-polymerized liposomes.

The development of clickable polymerizable liposomes presents many challenges as the click chemistry between the molecular handles (ethynyl groups) and the moieties of interest with an azido group may not be compatible with the poly-diacetylene backbones of the clickable polymerized liposomes. Moreover, the use of conventional Cu(I) catalysts for click reaction causes oxidative degradation of unsaturated carbon-carbon bonds in liposomes, including the polydiacetylene backbones, typically leads to a leakage of the clickable polymerized liposome.

Click reactions performed with some of these materials have been reported (Binder 2007, Cavalli 2006, Gupta 2005, Hassane 2006, Lutz 2004, Opsteen 2007, Wang 2003) but the reactions were mostly performed in solvents containing at least one organic solvent such as ethanol, isopropanol, DMSO, or DMF. For the few examples of using click reactions to modify these materials in aqueous solutions, the reported catalysts (Chan 2004, Rodionov 2007) were less efficient than our catalysts based on the copper complex of the ligands 1-5 (Figure X) which are soluble in water.

SUMMARY

According to some embodiments, the present invention provides compositions and methods for making multifunctional polymerized liposomes made from clickable polymerized liposome via the use of "molecular handles" such as azido and ethynyl groups on the liposome surface, thus combining liposome stability with click chemistry efficiency and versatility. The use of such clickable polymerized liposomes also helps ensure batch-to-batch reproducibility, eases the control of the size and density of the functional groups, as well as the composition and density of the resulting multifunctional liposomes.

According to some embodiments, the present invention provides compositions and methods for making and using multifunctional polymerized liposomes finding relevant application in medical sciences, particularly in bioimaging, diagnostics, drug delivery, and drug formulation. The compositions and methods involve lipids that are both polymerizable and have a "clickable" group that provides the ability to functionalize via a click reaction with various functional moieties useful for the above-listed applications. A catalyst is provided that allows the click reaction to proceed while being compatible with the backbones imparting polymerizability.

BRIEF DESCRIPTION OF THE DRAWINGS

The foregoing summary as well as the following detailed description will be better understood when read in conjunction with the appended drawings. It should be understood, however, that the present invention is not limited to the precise arrangements and instrumentalities shown herein. The components in the drawings are not necessarily to scale, emphasis instead being placed upon clearly illustrating the principles of the present invention. Moreover, in the drawings, like reference numerals designate corresponding parts throughout the several views.

The invention may take physical form in certain parts and arrangement of parts. For a more complete understanding of the present invention, and the advantages thereof, reference is now made to the following descriptions taken in conjunction with the accompanying drawings, in which.

DETAILED DESCRIPTION

According to some embodiments, the present invention is a method for making and using multifunctional polymerized liposomes prepared from clickable polymerized liposomes using click chemistry. The simultaneous and direct attachment of the desired molecules onto the liposome surface is achieved through small molecular handles such as ethynyl groups unprotected or protected with organosilyl groups or other groups or azido groups that are attached onto the liposome surface with or without a spacer, such as but not limited to biocompatible oligo- or poly(ethylene glycol).

Figure 1:
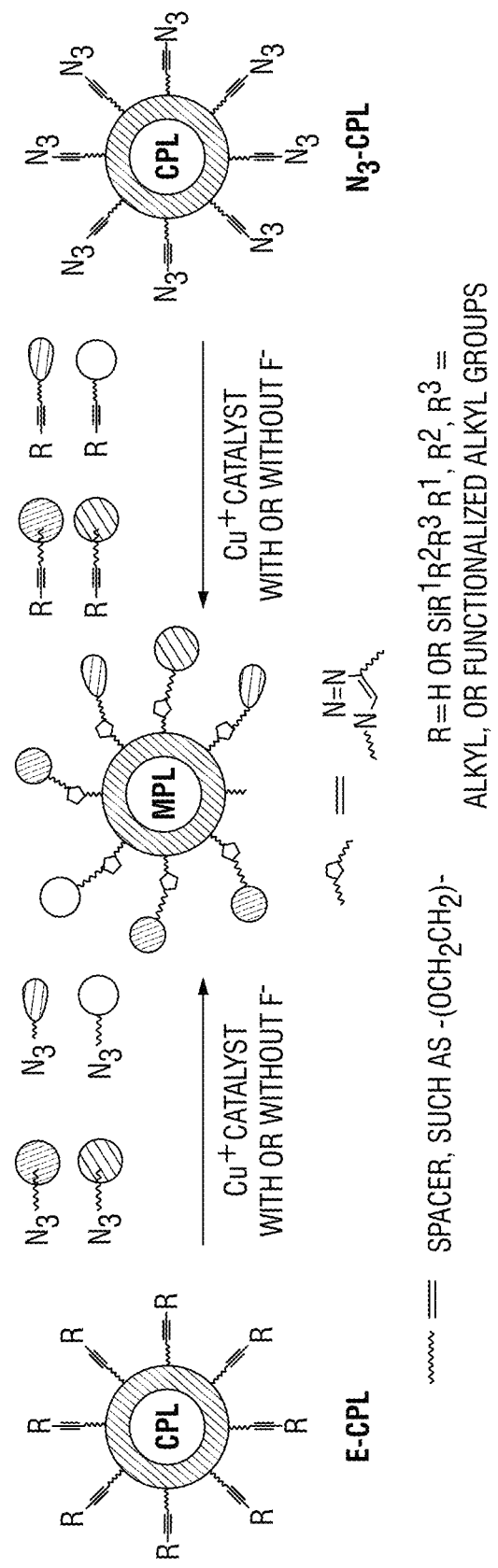
FIG. 1 is an illustration of the preparation of robust multi-functional polymerized liposomes using clickable polymerizable liposomes (CPL), from either an ethynyl-functionalized clickable polymerized liposome (E-CPL), or an azido-functionalized clickable polymerized liposome ($N_3$-CPL), followed by click reactions with ethynyl- and azido-functionalized moieties, respectively, in the presence of a copper catalyst.

FIG. 1 illustrates the preparation of multifunctional polymerized liposomes from clickable polymerized liposomes starting with either ethynyl-functionalized clickable polymerized liposome (E-CPL) or azido-functionalized clickable polymerized liposome ($N_3$-CPL), and followed by click reactions with the respective ethynyl or azido functionalized moieties.

Clickable polymerized liposomes containing lipids of the general formula $R^1$—$(CH_2)_m$—$\equiv$—$\equiv$—$(CH_2)_n$—$R^2$, wherein $R^1$ and $R^2$ are alkyl or other organic groups containing at least one ethynyl group and/or azido groups, m, n=1-30 are prepared. The ethynyl group may or may not be protected with organosilyl groups or other groups. Two or more of the lipid chains can be covalently joined. These lipids, which contain the clickable handles (azido or ethynyl groups) are mixed with other diacetylene lipids and/or other filler molecules, and are proceeded to produce clickable polymerized liposomes as illustrated by examples herein.

The surface density of the clickable handles (ethynyl or azido groups) on clickable polymerized liposomes is controlled by the ratio of the matrix diacetylene lipid and the clickable diacetylene lipid.

We herein demonstrate a new, robust platform containing molecular handles for covalent tethering of a wide variety of functional moieties through "click" reactions.

The most widely used "click" reaction involves [2+3] clycloaddition of an azido group with a terminal alkyne under mild conditions.

The click reaction successfully works on lipids containing polydiacetylene. The reaction runs rapidly in the presence of catalyst $Cu^+$. The catalytic reaction is further greatly accelerated in the presence of a so-called Fokin-Sharpless ligand as described in Chan T R, Hilgraf R, Sharpless K B, Fokin V V. Polytriazoles as Copper(I)-stabilizing ligands in catalysis. *Org. Lett.* 2004; 6: 2853-2855 that we have further chemically modified to make that catalyst soluble in water and biocompatible. Herein we claim modified Fokin-Sharpless ligands, such as (5), wherein oligo- or poly-(ethylene glycol) groups containing 4-500 ethylene glycol monomeric units are introduced.

Figure 7:
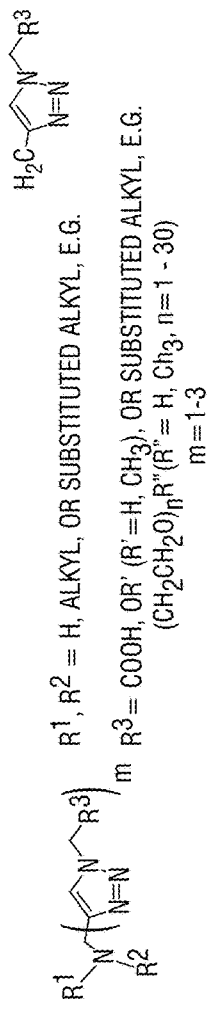
FIG. 7 shows a general formula for water soluble ligands of Cu(I)
Figure 8:
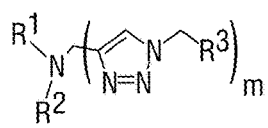
FIG. 8 shows exemplary water soluble ligands (6-10) of Cu(I)
Figure 8:
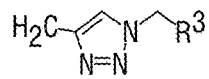
Figure 8:
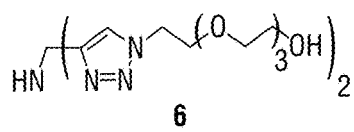
Figure 8:
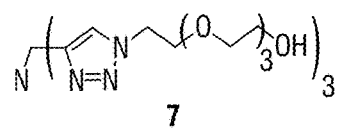
Figure 8:
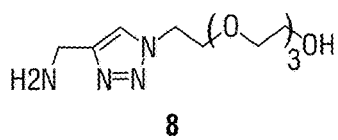
Figure 8:
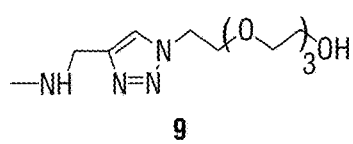
Figure 8:
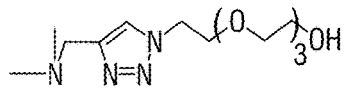

According to some embodiments, the present invention provides newly developed water-soluble Cu(I)-ligand complexes, in which the ligands have the general formula (shown in FIG. 7) with specific examples, ligands 6-10 (FIG. 8). The catalysts are contemplated to promote the click reaction in aqueous solutions for a wide range of materials, including but not limited to liposomes including polymerized liposomes, microbubbles, nanoparticles including metal and semiconductor nanoparticles and polymer nanoparticles, proteins, and cells including live cells. All these materials are modified with terminal alkynes with or without protecting groups, or azido groups.

Figure 10:
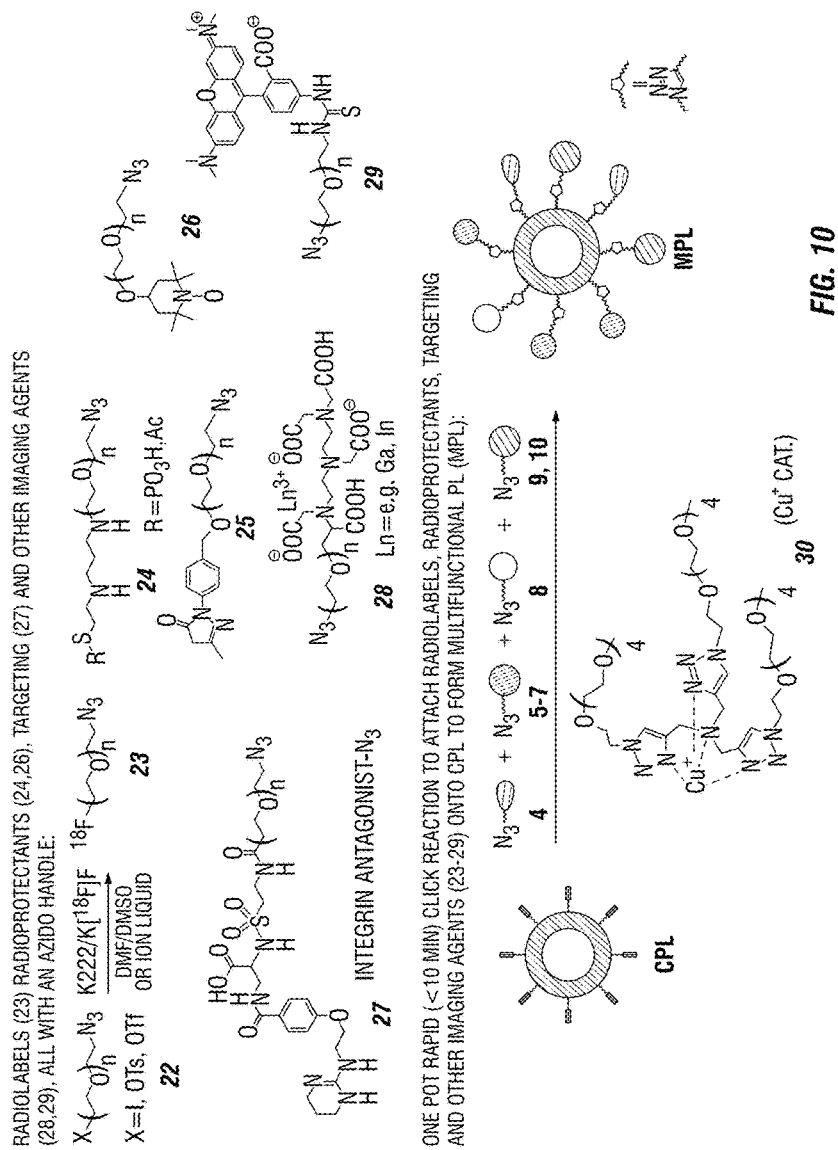
FIG. 10 shows exemplary functional moieties.

Suitable functional moieties are proteins, imaging agents, targeting agents, ligands, combinations thereof, and the like. For example, referring to FIG. 10, the following azides (23-29) can be tethered to the ethynyl-presenting clickable polymerized liposomes (CPL) via a click reaction to form the multifunctional polymerized liposome (MPL, FIG. 10). The azides may include the radiolabels 23 for PET imaging, the radioprotectants (24-26), the peptidomimetic antagonist 27 for selective targeting $\alpha_v\beta_3$ integrins with nM affinity, lanthanide complexes (e.g. 28) for multi-modality (MRI, SPECT, CT) imaging, and optical imaging agents (e.g. 29). The MPL can be optimized for their specificity, probe stability, and sensitivity. Localization of radiolabels on MPL increases imaging sensitivity but also promotes local radiolysis. To reduce damage of the probes by radiolysis, the azides 24-26 (analogues of well-known radioprotectants) may be attached to the liposome to locally scavenge the radicals from radiolysis. The time-dependent bleaching of fluorescence for the MPL labeled with 29 and varied ratio of 23 and the radioprotectants 24, 25, or 26 indicate the extent of radiolysis and the effectiveness of the radioprotectants. We can also monitor the scavenging process on MPL with varied ratio of 23 and 26 by MRI.

In one aspect, embodiments of the present disclosure relate to methods for the synthesis and use of clickable polymerized liposomes and multifunctional polymerized liposomes with a diameter in the range of 10 to 1,000 nanometers. More specifically, the methods disclosed herein make use of polymerized liposomes and well-defined molecules on the liposomes' surface for the direct and simultaneous attachment of a wide variety of various chemical and biochemical functional moieties such as imaging agents and targeting molecules. The resulting multifunctional polymerized liposomes can find use in many applications including, but not limited to bioimaging, diagnostics, drug delivery, and drug formulation.

In some aspects, embodiments disclosed herein relate to a method for making and using multifunctional polymerized liposomes from clickable polymerized liposomes. This method finds important applications, particularly in bioimaging, diagnostics, drug delivery, and drug formulation.

Thus, according to some embodiments a lipid comprises a clickable diacetylene lipid, comprising a clickable handle selected from the group consisting of ethynyl group and azide groups. The clickable diacetylene lipid may have the general formula $R^1-(CH_2)_m-\equiv-\equiv-(CH_2)_n-R^2$, wherein $R^1$ and $R^2$ are organic groups, at least one containing at least one chosen from an ethynyl group and an azido group.

According to some embodiments, a liposome comprises a plurality of lipids, wherein the plurality comprises a first plurality of matrix diacetylene lipids and a second plurality of clickable diacetylene lipids each lipid comprises a clickable diacetylene lipid, comprising a clickable handle selected from the group consisting of ethynyl group and azide groups. The clickable diacetylene lipid may have the general formula $R^1-(CH_2)_m-\equiv-\equiv-(CH_2)_n-R^2$, wherein $R^1$ and $R^2$ are organic groups, at least one containing at least one chosen from an ethynyl group and an azido group. According to some embodiments, a liposome comprises the polymerize product of the above-described liposome.

According to some embodiments, a multifunctional polymerized liposome comprises: a scaffold comprising a core polymerized liposome; a plurality of linkages attached to the scaffold; and a plurality of functional moieties, each attached to a linkage, wherein the linkages are each the reaction product of a click reaction with at least one of an ethynyl group and an azido group. Each linkage may comprise a triazo group. The functional moieties may comprise a first plurality of first functional moieties and the second plurality of second functional moieties and wherein the ratio of the first plurality to the second plurality is predetermined. The multifunctional polymerized liposome may comprise the clicked polymerized product of matrix diacetylene lipids and a plurality of clickable diacetylene lipids each comprising a clickable handle selected from the group consisting of ethynyl group and azide groups, wherein the linkages are derived from the clickable handles. The multifunctional polymerized liposome may contained in one of a bioimaging agent, a diagnostic agent, a drug delivery vehicle, and a drug formulation.

According to some embodiments, a catalyst comprises Cu(I); and a water soluble ligand, wherein the water soluble ligand has the general formula shown in FIG. 7.

According to some embodiments, a method for making multifunctional polymerized liposomes comprises the steps of mixing lipids of the general formula $R^1-(CH_2)_m-\equiv-\equiv-(CH_2)_n-R^2$, wherein $R^1$ and $R^2$ are organic groups containing at least one chosen from an ethynyl group and an azido group, so as to form a lipid solution, wherein m and n are integers that vary independently from 1-30; treating the lipid solution so as to form clickable liposomes; polymerizing the clickable liposomes by cooling and UV light irradiation; functionalizing the polymerized clickable liposomes with the at least one chosen from an azido group and an ethynyl group in the presence of a catalyst for the click reaction.

The catalyst may comprise copper and a water soluble ligand. The water soluble ligand may have the general formula shown in FIG. 7. The ethynyl group may be protected with a removable protecting group. The lipids may adapted to be covalently joined. The method may further comprise the step of adding additional molecules chosen from lipids, peptides, polymers, sterols and substituted oxysterols. The lipid may further comprise a biocompatible head group chosen from oligo (ethylene glycols) and poly(ethylene glycols). The surface density of the ethynyl or azido groups on the polymerized clickable liposomes may be controlled by the ratio of a matrix diacetylene lipid and a clickable diacetylene lipid. The method treating may comprise sonicating. Alternately or in combination, the treating may comprise extruding.

According to some embodiments, a bioimaging agent comprises a multifunctional polymerized liposomes made by the above-described method.

According to some embodiments, a diagnostic agent comprises a multifunctional polymerized liposomes made by the above-described method.

According to some embodiments, a drug delivery vehicle comprises a multifunctional polymerized liposomes made by the above-described method.

According to some embodiments, a drug formulation comprises a multifunctional polymerized liposomes made by the above-described method.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLES

Example 1. Preparation of Clickable Polymerized Liposomes

Figure 2:
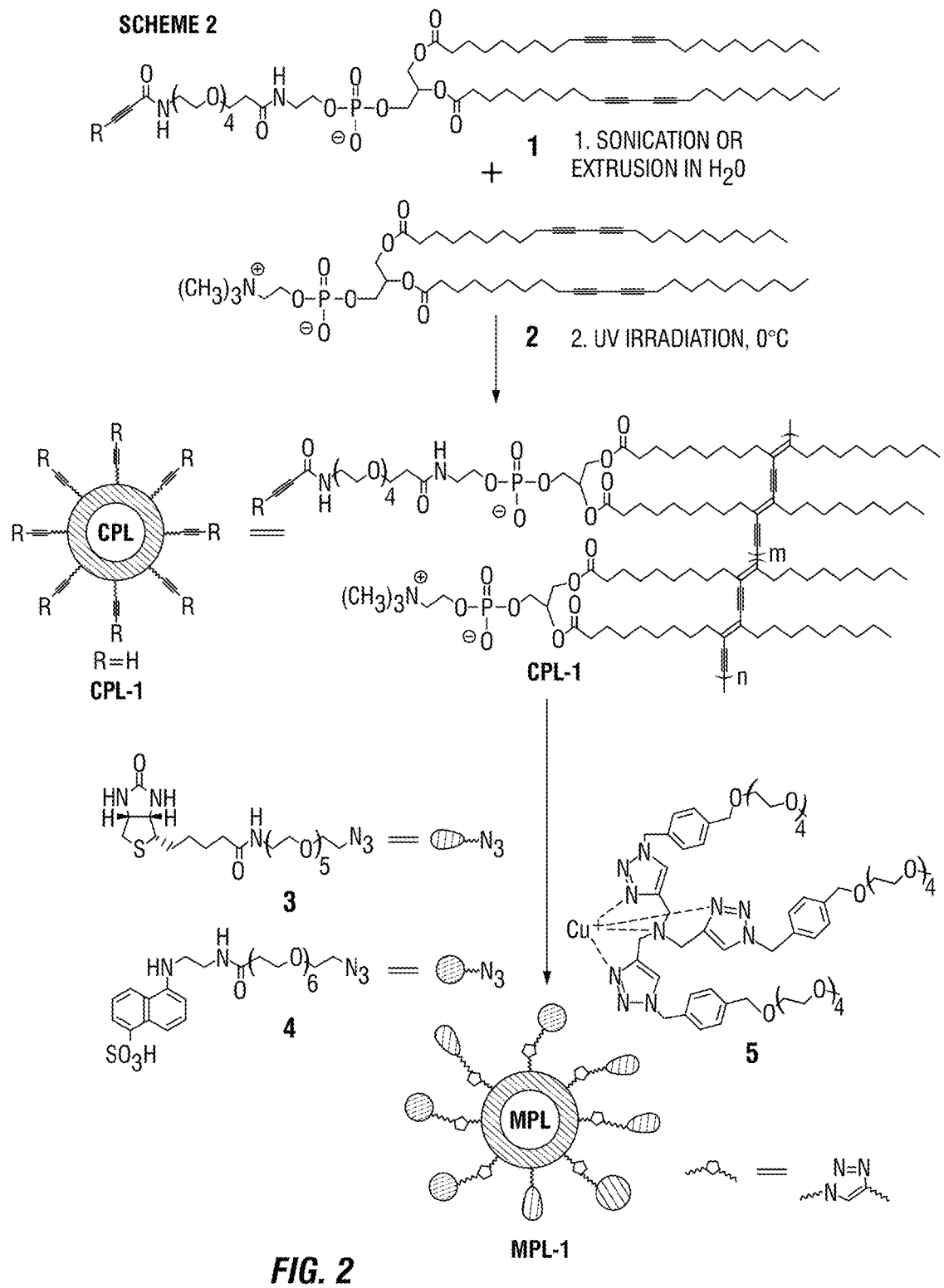
FIG. 2 illustrates the synthesis scheme of clickable polymerized liposomes from lipid (1) and lipid (2). The next step consists in making the multifunctional polymerized liposomes through click chemistry using molecules of interests such as compounds (3) and (4) and a catalyst (5)

FIG. 2 illustrates the synthesis scheme of clickable polymerized liposomes from lipid (1) and lipid (2). The next step was making the multifunctional polymerized liposomes through click chemistry. In this example, the present inventors demonstrate the concept using molecules as the biotin (3) and the fluorophore (4) in the presence of the catalyst (5). The biotin ligand 3 was to demonstrate the targeting ability of the multifunctional polymerized liposomes, and the fluorophore 4 serves to demonstrate the incorporation of imaging agent. Both of 3 and 4 have an azido group for tethering to the clickable liposome via click reaction in the presence of the water soluble catalyst 5 as described below.

The diacetylene lipids tethering an ethynyl groups (1) was synthesized as described in Example 4. Compound (1) was mixed with the lipid (2) as the matrix in $CHCl_3$/MeOH 9:1. After evaporation of the solvent, Millipore water preheated to 80° C. is added and the mixture is sonicated either in a probe sonicator or a sonication bath, with or without extrusion over a 100 nm membrane. The solution was placed in a Petri dish sitting on an ice bed, and irradiated with a handhold UV lamp for 20-100 minutes. The resulting red or orange or greenish colored solutions or suspensions were filtered over a 0.2 mm filter.

Figure 3:
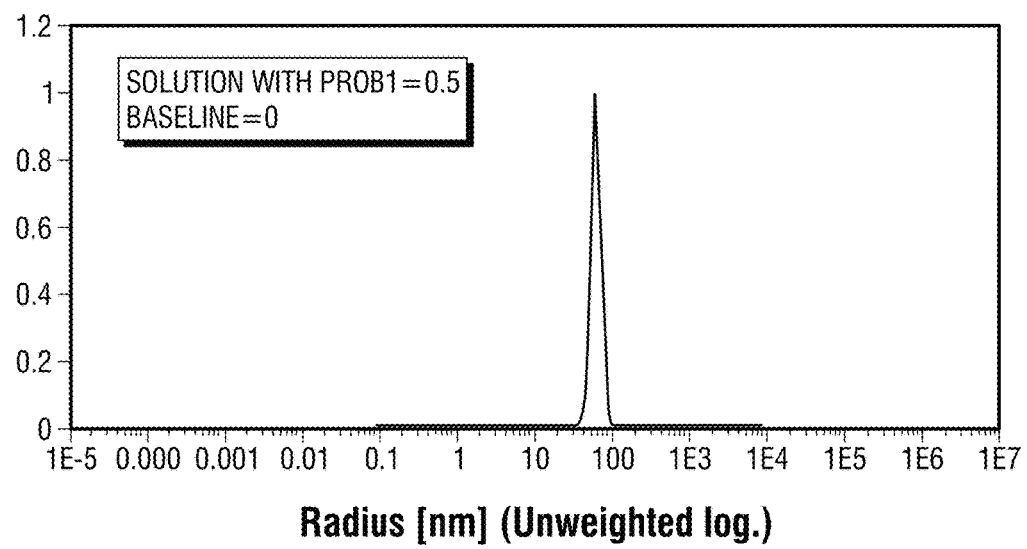
FIG. 3 shows dynamic light scattering diagram of clickable polymerized liposomes prepared by extrusion of a 10 mM (based on lipid chains) solution of 1/2 (1:9). ALV-Correlator Distribution Function Fit result: 99.84% weight of peak at 114±22 nm.

FIG. 3 results from dynamic light scattering measurement and shows that the average particle size of clickable polymerized particle was 114±22 nm.

Figure 4:
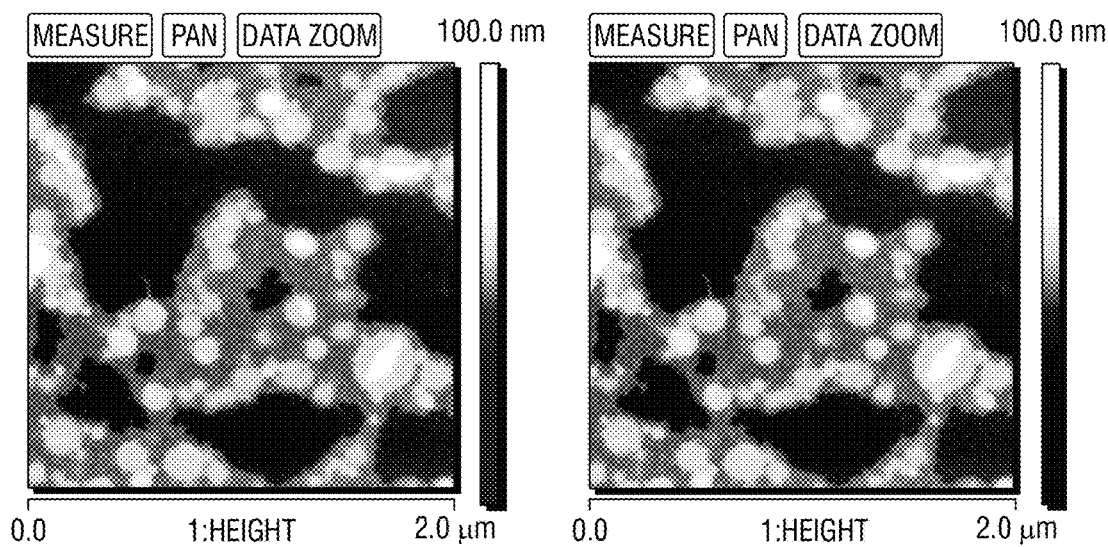
FIG. 4 shows tapping mode AFM images of clickable polymerized liposomes prepared by extrusion of a 10 mM (based on lipid chains) solution of 1/2 (1:9)

FIG. 4 shows a typical atomic force microscopy imaging of clickable polymerized particles in tapping mode. The sample was prepared by diluted the resulted clickable polymerized liposome solution 5 times. About 50 ml of that solution was dropped onto freshly cleaved mica. After the solution dried, the sample was visualized using a multimode AFM (Veeco). AFM images were obtained using a commercial silicon tip (NSC35/No Al, MikroMasch) in tapping mode in air. The scan was performed at 1 Hz, and the images were captured in 512×512 pixel format. Results from both light scattering measurements and atomic force microscopy show that the particle size was in the order of 100 nm.

Langmuir trough experiments were performed at different ratios of clickable clickable diacetylene lipid, such as compound (1), to matrix diacetylene lipid such as compound (2), to ensure the miscibility of the two lipids. The clickable liposomes were prepared by removal of the organic solvent from the mixture by evaporation in a rotavap, and the residue was dried in a vacuum pump. The lipid mixture was then hydrated to a known lipid density (e.g. 5 mM acyl chain) using warm (up to 80° C.) aqueous buffer or deionized water. The resulting suspension was then sonicated at temperatures above the phase transition using a sonication bath or probe-tip sonicator. After two minutes of sonication, a milky suspension was formed. The size of the unpolymerized liposomes can be controlled by extrusion following the well-known procedure.

The liposomes were then polymerized by cooling the liposome solution (either extruded or non-extruded) to 0-4° C. on a Petri dish sitting on an ice bath followed by irradiating the solution at 254 nm with a hand-held UV lamp sitting one cm above the solution. The resulting polymerized liposomes were yellow-orange in color.

Example 2. Preparation of Multifunctional Polymerized Liposomes Via Click Chemistry Reactions To demonstrate the facile preparation of multifunctional polymerized liposomes, the present inventors used a biotin derivative, such as compound (3) and a fluorophore such as compound (4), both tethering an azido group, to react with the clickable polymerized liposomes in the presence of a catalyst such as compound (5). After reaction at ambient conditions in aqueous solution for 14 hours, the mixture was subjected to dialysis against water for 24 hours and then PBS buffer for another 24 hours.

Figure 5:
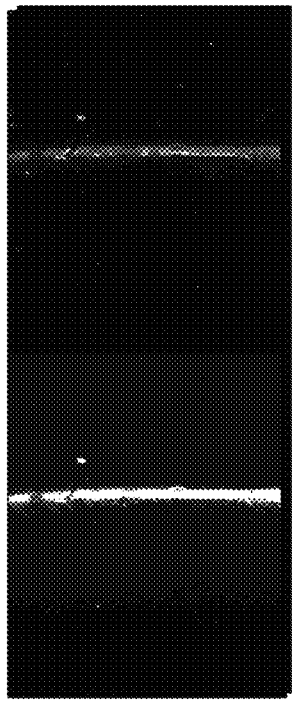
FIG. 5 represents fluorescence images of FITC-labeled avidin absorbed on the microstructure generated on OEG monolayer upon treatment with MPL-1 containing both biotin and a blue-fluorescent dye with a filter for FITC (left) and DAPI (right)

Example 3. Targeted Imaging of Multifunctional Polymerized Liposomes Prepared from Clickable Polymerized Liposomes To demonstrate that the multifunctional polymerized liposome MPL-1 prepared from the clickable polymerized liposome CPL-1 (as illustrated in FIG. 2) can successfully be used for targeted imaging of avidin, micro-structures of avidin labeled with a fluorescent dye different from the one on MPL-1 were prepared. The structures were prepared on OEG monolayers on silicon. A sample was immersed in a solution of MPL-1 for 30 min at room temperature, washed with Millipore water and dried with a flow of argon. Fluorescence microscopy was performed over two filters (DAPI for the dye molecule on MPL and FITC for the fluorophore on avidin) with a 60× objective. As illustrated in FIG. 5, MPL-1 containing biotin only absorbed onto avidin-presenting patterns (green structure in the left image). The presence of the dye on MPL-1 is indicated by the blue fluorescent shown in the right image. The same experiment was performed with MPL without biotin and dye, prepared from CPL-1 using the same procedure for MPL-1 but in the absence of the catalyst Cu(I). In this case, the adsorption of MPL onto avidin patterns did not occur. The attachment of multiple functional moieties such as biotin and dye molecules onto CPL via click chemistry was therefore successful.

Example 4. Synthesis 4.1 Synthesis of Lipid (1)

Figure 6:
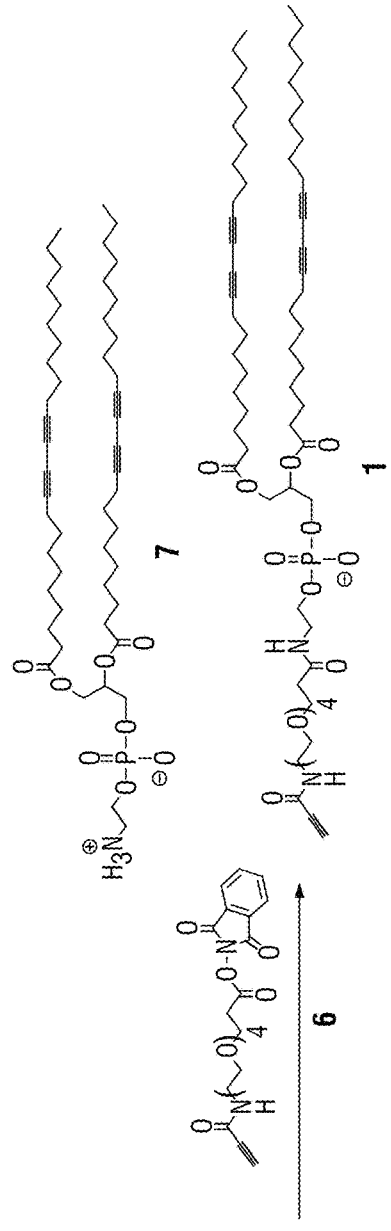
FIG. 6 shows a synthesis of lipid (1)

A synthesis of lipid (1) is illustrated schematically in FIG. 6. Lipid (1) is exemplary of a clickable diacetylene lipid.

Tert-Butyl 3-oxo-7,10,13,16-tetraoxa-4-azanonadec-1-yn-19-oate was prepared as follows. HOBt (151 mg, 1.12 mmol), Et$_3$N (113 µL, 1.12 mmol), and EDC (215 mg, 1.12 mmol) was added to a solution of 3-(trimethylsilyl)propiolic acid (159 mg, 1.12 mmol) in THF (1 mL). A solution of tBuOOCCH$_2$CH$_2$(OCH$_2$CH$_2$)$_4$—NH$_2$ (300 mg, 0.93 mmol) in THF (2 mL) was added, and the reaction mixture was stirred overnight. The mixture was then diluted with CH$_2$Cl$_2$ (10 mL) and the organic phase was washed with 5% KF (3×5 mL) and dried over Na$_2$SO$_4$. The solvent was removed in vacuo, and the residue was purified by silica gel column chromatography to give the product (309 mg, 0.83 mmol, 89%) as colourless viscous liquid. $^1$H NMR (300 MHz, CDCl$_3$) δ 7.37 (d, 2H, J=8.0 Hz), 7.30 (d, 2H, J=8.2 Hz), 4.58 (s, 2H), 4.33 (s, 2H), 3.69-3.58 (m, 14H), 3.56-3.52 (m, 2H), 3.37 (s, 3H); $^{13}$C NMR (75 MHz, CDCl3) δ 138.6, 134.7, 128.3, 128.2, 72.9, 72.0, 70.7, 70.6, 70.5, 69.7, 68.0, 59.1, 54.6; MS (ESI) m/z calculated for C$_{18}$H$_{31}$NO$_7$ [M+H]$^+$ 374.2 found [M+Na]$^+$ 396.2.

Compound (6) was prepared as follows. A solution of tert-Butyl 3-oxo-7,10,13,16-tetraoxa-4-azanonadec-1-yn-19-oate (250 mg) in THF (3 mL) was treated with NHP (250 mg) and DIC (150 mg). The mixture was stirred overnight at room temperature. The solvent was removed in vacuo, and the residue purified by silica gel column chromatography to give the product as a light yellow viscous liquid, which was directly used for the next step.

Lipid (1) was prepared as follows. To a solution of compound (7) (35 mg, 0.03 mmol) in CH$_2$Cl$_2$ (1 ml) was added compound (6) (27.2 mg, 0.06 mmol). The reaction was stirred overnight at room temperature. The solvent was removed in vacuo, and the residue purified by silica gel column chromatography to give the desired compound (1, 20.0 mg, 0.2 mmol, 67%) as colorless solid. $^1$H NMR (300 MHz, CDCl$_3$) δ 4.42 (m, 1H), 4.24-4.16 (m, 2H), 4.00-3.96 (m, 2H), 3.78-3.65 (m, 22H), 2.5 (m, 2H), 2.33-2.25 (m, 8H), 1.60-1.24 (m, 54H), 0.92 (t, 6H, J=7.7 Hz).

Biotin-EG$_6$N$_3$ or compound (3) was prepared as follows. Biotin-NHS (0.21 g, 0.60 mmol) was added to a solution of NH$_2$-EG$_6$-N$_3$ (0.15 g, 0.50 mmol) and diisopropylethylamine (0.10 mL, 0.60 mmol) in THF (15 mL). The reaction mixture was stirred overnight at room temperature and under N$_2$ atmosphere. The solvent was evaporated in vacuo. The crude product was purified by column chromatography to yield pure biotin-EG$_6$N$_3$ (3, 0.37 g, 0.47 mmol, 79%) as a clear viscous oil. $^1$H NMR (300 MHz, CDCl$_3$) δ 7.30 (d, 2H, J=8.2 Hz), 4.58 (s, 2H), 4.33 (s, 2H), 3.69-3.58 (m, 14H), 3.56-3.52 (m, 2H), 3.37 (s, 3H); $^{13}$C NMR (75 MHz, CDCl3) δ 173.3, 164.2, 70.3, 70.2, 70.1, 69.9, 69.8, 69.6, 61.6, 60.1, 55.6, 50.4, 40.3, 38.9, 35.7, 28.2, 27.9; MS (ESI) ink calculated for C$_{22}$H$_{40}$N$_6$O$_7$S [M+H]$^+$ 533.2 found [M+Na]$^+$ 355.3.

5-(1-azido-21-oxo-3,6,9,12,15,18-hexaoxa-22-azatetracosan-24-ylamino)naphthalene-1-sulfonic acid or compound (4) was prepared as follows. HOBt (51.5 mg, 0.37 mmol), Et$_3$N (77.2 µL, 0.56 mmol), and EDC (106.2 mg, 0.56 mmol) are added to 1-azido-3,6,9,12,15,18-hexaoxa-henicosan-21-oic acid (212.2 mg, 0.56 mmol) in DMF (1 mL). Then, 5-(2-aminoethylamino)naphthalene-1-sulfonic acid (100 mg, 0.37 mmol) in DMF (1 mL) is added, and the reaction mixture is stirred 24 h. The solvent was removed in vacuo, and the residue purified by silica gel column chromatography to give the desired compound (4), 194.4 mg, 0.31 mmol, 85%) as colorless liquid. $^1$H NMR (300 MHz, $D_2O$) δ 8.03-7.88 (m, 3H), 7.39-7.29 (m, 2H), 6.49 (d, 1H, J=7.7 Hz), 3.65-3.50 (m, 22H) 3.46-3.33 (m, 2H), 3.22-3.10 (m, 2H), 2.35-2.25 (m, 2H).

4.2. Synthesis of the Ligand for the Catalyst (5)

1-(4-(chloromethyl)phenyl)-2,5,8,11,14-pentaoxapentadecane. To a solution of tetraethylene glycol monomethyl ether (2.00 g, 9.61 mmol) in THF (15 mL) at room temperature was added NaH (276.7 mg, 11.53 mmol). The reaction mixture was stirred for 30 min, followed by the addition of 1,4-bis(chloromethyl)benzene (2.01 g, 11.5 mmol). The reaction mixture was stirred at room temperature overnight and subsequently the solvent was evaporated. The reaction mixture was then dissolved in $CH_2Cl_2$ and washed with water. The organic phase was dried with $Na_2SO_4$ and concentrated in vacuo. The residue was purified using silica gel column chromatography to give the desired compound (2.56 g, 7.40 mmol, 77%) as a colorless liquid. $^1$H NMR (300 MHz, $CDCl_3$) δ 7.26-7.40 (m, 4H), 4.55 (s, 2H), 4.54 (s, 2H), 3.69-3.56 (m, 14H), 3.53-3.50 (m, 2H), 3.34 (s, 3H); $^{13}$C NMR (75 MHz, CDCl3) δ 138.7, 136.8, 128.7, 128.0, 72.8, 71.9, 70.7, 70.6, 70.5, 69.6, 59.1, 46.1; MS (ESI) m/z calculated for $C_{22}H_{35}N_6O_{11}$ [M+H]$^+$ 347.1 found [M+H$_2$O]$^+$ 364.2.

1-(4-(azidomethyl)phenyl)-2,5,8,11,14-pentaoxapentadecane. To a solution of 1-(4-(chloromethyl)phenyl)-2,5,8,11,14-pentaoxapentadecane (1.50 g, 4.33 mmol) in DMF (10 mL) was added NaN$_3$ (337.9 mg, 5.20 mmol). The reaction mixture was stirred overnight at 110° C. The solvent was subsequently evaporated. The residue was then suspended in ethyl acetate and filtered. The filtrate was concentrated in vacuo. The residue was purified by silica gel column chromatography to give the desired azide (1.53 g, 4.33 mmol, 90%) as a colorless liquid. $^1$H NMR (300 MHz, CDCl$_3$) δ 7.37 (d, 2H, J=8.0 Hz), 7.30 (d, 2H, J=8.2 Hz), 4.58 (s, 2H), 4.33 (s, 2H), 3.69-3.58 (m, 14H), 3.56-3.52 (m, 2H), 3.37 (s, 3H); $^{13}$C NMR (75 MHz, CDCl3) δ 138.6, 134.7, 128.3, 128.2, 72.9, 72.0, 70.7, 70.6, 70.5, 69.7, 68.0, 59.1, 54.6; MS (ESI) m/z calcd for $C_{17}H_{27}N_3O_5$ [M+H]$^+$ 353.2 found [M+H$_2$O]$^+$ 371.2.

tris((1-(4-2,5,8,11,14-pentaoxapentadecylbenzyl)-1H-1,2,3-triazol-4-yl)methyl)amine. Tripropargylamine (82.4 mg; 0.63 mmol) in acetonitrile (1 mL) was treated sequentially with 1-(4-(azidomethyl)phenyl)-2,5,8,11,14-pentaoxapentadecane (1.00 g, 2.83 mmol), 2,6-lutidine (67.4.mg, 0.63 mmol), and Cu(MeCN)$_4$PF$_6$ (1.3 mol % with respect to total alkyne units). After the mixture was stirred at room temperature for 3 days, the solvent was evaporated, and the residue purified using silica gel column chromatography to give the desired ligand (0.56 g, 0.47 mmol, 74%) as a light brown viscous liquid. $^1$H NMR (300 MHz, CDCl$_3$) δ 7.74 (s, 3H), 7.33 (d, 6H, J=7.8 Hz), 7.25 (d, 6H, J=8.1 Hz), 5.48 (s, 6H), 4.54 (s, 6H), 3.74-3.52 (m, 48H), 3.37 (s, 3H); $^{13}$C NMR (75 MHz, CDCl3) δ 170.8, 152.2, 80.5, 77.4, 73.3, 70.4, 70.2, 70.1, 69.1, 66.7, 39.5, 36.0, 27.9.

Example 5. Preparation of the Clickable Polymerized Liposome (CPL-1)

Compound (1) (5 mg) was mixed with lipid (2) (25 mg) as the matrix in CHCl$_3$/MeOH (10 mL, v/v=9:1). Millipore water preheated to 80° C. (5 mL) was added after evaporation of the solvent. The mixture was sonicated in a sonication bath for two minutes and to form a milky suspension. One mL solution was taken out using an Avanti syringe and extruded for 21 times using an Avanti Mini-Extruder with a 100 nm membrane at 80° C. The solution was then placed in a Petri dish sitting on an ice bed, and irradiated with a handhold 254 nm UV lamp (Model UVLS-28, UVP) for 45 min. The resulting orange colored solution was filtered over a 0.2 mm filter and subject to light scattering and AFM imaging.

Example 6. Attachment of Compounds (3) and (4) to CPL-1 Via Click Chemistry Reaction To a solution of clickable polymerizable liposome (CPL-1, 5 mg, ca. 0.01 mmol of ethynyl group) in water (25 ml) was added compound (4) (31.0 mg, 0.05 mmol). The copper catalyst 5 was formed in situ by sequential addition to the solution of copper sulphate (0.01 eq. of ethynyl groups), tris((1-(4-2,5,8,11,14-pentaoxapentadecylbenzyl)-1H-1,2,3-triazol-4-yl)methyl)amine (0.01 eq. of ethynyl groups), and ascorbic acid (0.2 eq. of ethynyl groups). The reaction was stirred overnight at room temperature. The reaction mixture was then purified by dialysis against water for 48 h.

Example 7. Preparation of Avidin Microstructures on OEG Monolayers on Si(111)

Commercial silicon wafers are cleaned using Piranha solution. After washed with Millipore water, the samples are dipped into NH$_4$F solution (Sigma-Aldrich) for 20 minutes under argon environment, then washed with Millipore water followed by drying with a flow of argon. The film is put into a home-made vacuum chamber, with a drop of neat CH$_3$(OCH$_2$CH$_2$)$_7$(CH$_2$)$_8$CH=CH$_2$ on the upper quartz window. After the chamber is vacuumed for about 10 minutes, the silicon substrate is allowed to be in contact with the alkene to form a thin and homogeneous layer between the substrate and the quartz window. The substrate is then illuminated with a hand-hold 254 nm UV-lamp (Model UVLS-28, UVP) for 2 hours, followed by washing with petroleum ether, CH$_2$Cl$_2$, and absolute ethanol, and finally drying with a stream of argon. After scratched with a sharp diamond pen, this sample is dipped into FITC-avidin solution (1 mg/mL, Sigma-Aldrich) for 30 min at room temperature, washed with Millipore water and dried with a flow of argon.

Example 8. Targeted Imaging of Multifunctional Polymerized Liposomes Prepared from Clickable Polymerized Liposomes The above avidin microstructured sample was immersed in a solution of MPL-1 for 30 minutes at room temperature, washed with Millipore water and dried with a flow of argon. This sample was imaged using fluorescence microscopy over two filters (DAPI for the dye molecule on MPL-1 and FITC for the avidin) with a 60× objective. As shown in FIG. 5, MPL-1 containing biotin only absorbed onto avidin-presenting patterns. The same experiment was performed with a control sample obtained by following the exact same condition to prepare MPL-1 from CPL-1, except that Cu(I) is not added. No adsorption of MPL-1 onto avidin patterns was observed. These results show that the attachment of functional moieties such as biotin molecules onto clickable polymerized liposomes via click chemistry reactions was successfully achieved.

Example 9. Testing of Catalysts with Water Soluble Ligands

Figure 9:
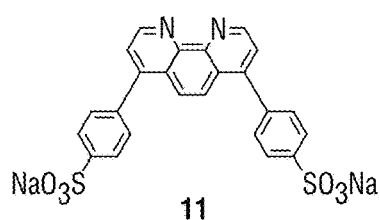
FIG. 9 shows a comparative ligand 11.
Figure 11:
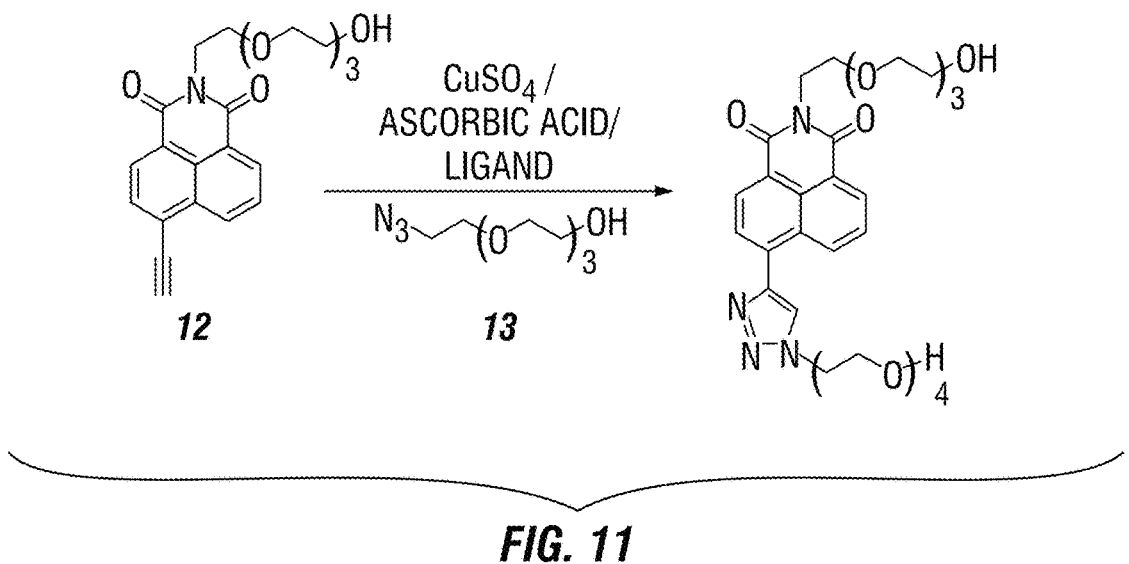
FIG. 11 shows a click reaction used for kinetic evaluation of catalysts shown in FIG. 8.

The catalysts shown in FIG. 7 were screened, both exemplary catalysts 6-10 and comparative catalyst 11. The click reaction shown in FIG. 11 using the alkyne 12 and the azide 13 forming the highly fluorescent product 14 was used for screening the catalysts. The reaction was completed in less than 30 min using our catalyst Cu(I)/1 while it took 3 hours to complete using the reported water-soluble catalyst Cu(I)/11. The catalyst Cu(I)/11 (FIG. 9) is a commercial (I) ligand (11 (Lewis 2004).

Figure 12:
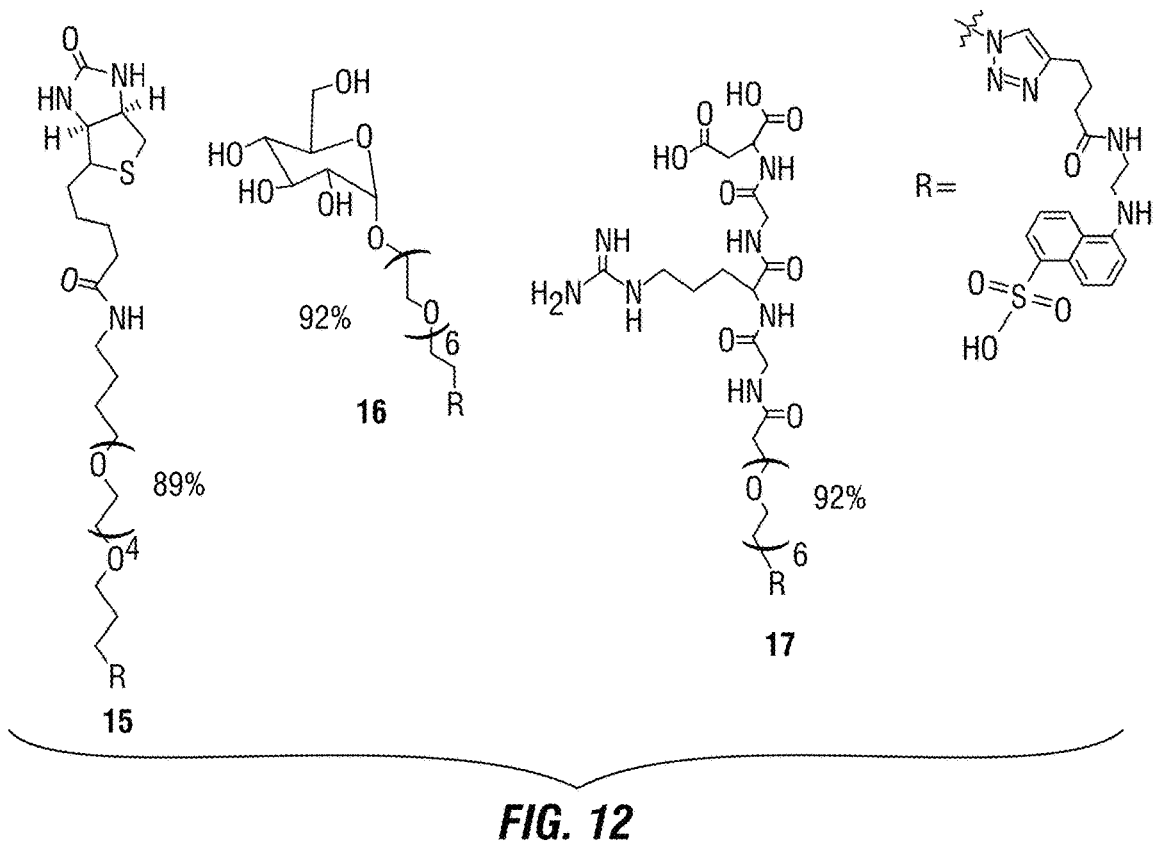
FIG. 12 shows exemplary products obtained by a click reaction in high yields in aqueous medium using ligand 6.
Figure 13:
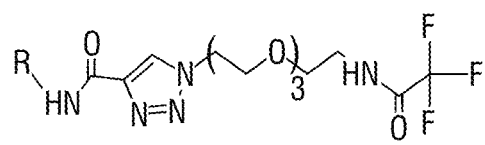
FIG. 13 shows exemplary products obtained by click reaction in high yields in organic medium using ligand 6.
Figure 13:
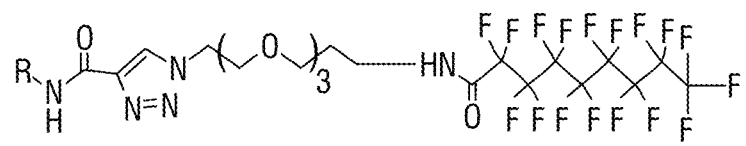
Figure 13:
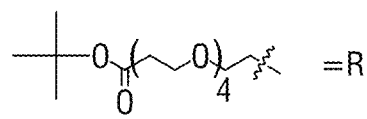

The catalyst Cu(I)/1 was used for the synthesis of compounds 15-17 (FIG. 12). The catalysts Cu(I)/1-5 can also be used in organic solvents to promote the click reaction, e.g. to provide compounds 18, 19 (FIG. 13).

Reaction Conditions Using 7 as the Ligand for Cu(I):

The overall volume in each vial was 250 µl containing a solution of 1,8-naphthalimide florpher 12 (0.5 mM), $OEG_4N_3$ 13 (1.0 mM), $CuSO_4$ (1.0-0.625 mM), Ligand 7 (2.0-0.5 mM), and sodium ascorbate (5.0-1.25 mM) in water 50 mM Hepes buffer (pH 7.2). The reactions were allowed to stand under ambient conditions (with no stirring) and the yields were monitored by fluorescence intensity (excitation, 365 nm; emission, 460 nm) using a Fusion plate reader (Perkin-Elmer/Packard, Wellesley, Mass.). HPLC is used to verify that the fluorescence intensity is proportional to the concentration of the product.

The reaction using $CuSO_4$ (1.0-0.5 mM), Ligand (2.0-0.1 mM), and sodium ascorbate (5.0-1.25 mM) finished in 4 hours.

The reaction using $CuSO_4$ (0.125 mM), Ligand (0.5 mM), and sodium ascorbate (5.0-1.25 mM) finished in 12 hours.

Results show that the best catalyst under ambient conditions is Cu(I)/ligand 2.

Reaction Conditions Using 6 as the Ligand for Cu(I) Under Anaerobic Conditions:

The overall volume in each vial was 250 µl containing a solution of 1,8-naphthalimide florpher 12 (0.5 mM), $OEG_4N_3$ 13 (1.0 mM), $CuSO_4$ (1.0-0.5 mM), Ligand 6 (2.0-1.0 mM), and sodium ascorbate (5.0-2.5 mM) in water 50 mM Hepes buffer (pH 7.2) subjected to 12 cycles of freeze-thaw. The reactions were allowed to stand under anaerobic conditions in an anaerobic chamber and in schlenk tube (with and without stirring) and the yields were monitored by fluorescence intensity (excitation, 365 nm; emission, 460 nm) using a Fusion plate reader (Perkin-Elmer/Packard, Wellesley, Mass.) HPLC is used to verify that the fluorescence intensity is proportional to the concentration of the product.

The reaction using $CuSO_4$ (1.0 mM), Ligand (2.0 mM), and sodium ascorbate (5.0-2.5 mM) finished in 2 hours when carried under anaerobic chamber without stirring.

The reaction using $CuSO_4$ (0.5 mM), Ligand (1.0 mM), and sodium ascorbate (2.5 mM) finished in 40 min when carried in a schlenk tube without stirring.

The reaction using $CuSO_4$ (0.5 mM), Ligand (1.0 mM), and sodium ascorbate (2.5 mM) finished in 30 min when carried in a schlenk tube with stirring.

Results show that the best catalyst under anaerobic conditions is Cu(I)/ligand 6.

General Procedure for Aqueous Phase Reaction

To a solution of 5-(2-hex-5-ynamidoethylamino)naphthalene-1-sulfonic acid in water (1.0 mL) at room temperature was added the catalyst (2, 2 mol %), $CuSO_4$ (1 mol %) and ascorbic acid (5 mol %). To the resulting mixture was added the biomolecule azide and it was stirred at room temperature overnight. The reaction mixture was concentrated in vacuo and the residue was purified by silica gel column chromatography.

General Procedure for Organic Phase Reaction

To a solution of tert-butyl 3-oxo-7,10,13,16-tetraoxa-4-azanonadec-1-yn-19-oate in acetonitrile (1 mL) at room temperature was added the catalyst (7, 2 mol %), $Cu(MeCN)_4PF_6$ (1 mol %). To the resulting mixture was added the azide and it was stirred at room temperature overnight. The reaction mixture was concentrated in vacuo and the residue was purified by silica gel column chromatography.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

What is claimed is:

1. A biocompatible catalyst for a Copper (I) Catalyzed Azide-Alkyne Cycloaddition click reaction for functionalizing polymerizable liposomes comprising:
   Cu(I); and
   a Cu(I) stabilizing ligand, wherein the Cu(I) stabilizing ligand comprises a water-soluble triazole or oligotriazole ligand comprising
   a ligand selected from the group consisting of

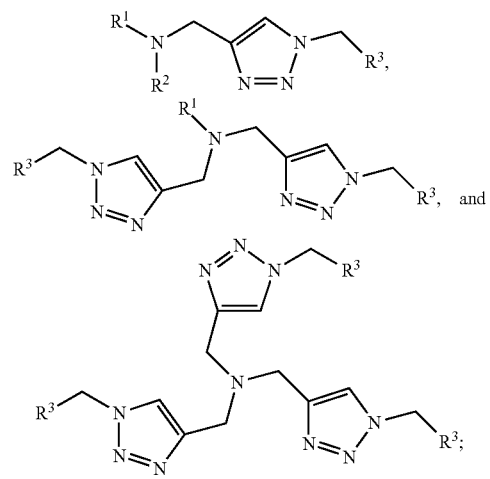

wherein $R^1$ is selected from the group consisting of H, alkyl, and substituted alkyl; wherein $R^2$ is selected from the group consisting of H, alkyl, and substituted alkyl; wherein $R^3$ is $(CH_2CH_2O)_nR''$, wherein n=1-30; and wherein R'' is selected from the group consisting of H and $CH_3$;

wherein the catalyst is formed by addition of the water soluble triazole or oligo-triazole ligand and ascorbic acid to copper sulfate, wherein the click reaction comprises:

functionalizing the polymerized clickable liposomes with at least one clickable group chosen from an azido group and an ethynyl group in the presence of the catalyst, and wherein the Cu(I) and the Cu(I) stabilizing ligand form a complex.

2. The catalyst according to claim 1, wherein the polymerized clickable liposomes are made by a method comprising:

mixing clickable lipids of the general formula $R^3$—$(CH_2)_p$—≡≡—$(CH_2)_n$—$R^4$, wherein $R^3$ and $R^4$ are organic groups containing at least one clickable group chosen from an ethynyl group and an azido group;

wherein p and n are integers that vary independently from 1-30;

treating the clickable lipid solution to form clickable liposomes;

polymerizing the clickable liposomes by cooling and UV light irradiation to form the polymerized clickable liposomes.

3. The catalyst according to claim 1, wherein the catalyst is formed in situ in the presence of the polymerized clickable liposomes.

* * * * *